(12) United States Patent
Dakshinamoorthy et al.

(10) Patent No.: US 9,650,345 B2
(45) Date of Patent: May 16, 2017

(54) PROCESS FOR THE PREPARATION OF PYRAZOLE DERIVATIVES

(71) Applicant: SRF LIMITED, Gurgaon (IN)

(72) Inventors: Srikant Dakshinamoorthy, Gurgaon (IN); Thangaselvam Kamaraj, Gurgaon (IN); Sarathy Iyengar, Gurgaon (IN); Arumugam Nagappan, Gurgaon (IN); Rahul Saxena, Gurgaon (IN); Rajdeep Anand, Gurgaon (IN)

(73) Assignee: SRF LIMITED, Gurgaon (IN)

( * ) Notice: Subject to any disclaimer, the term of this patent is extended or adjusted under 35 U.S.C. 154(b) by 0 days.

(21) Appl. No.: 15/144,432

(22) Filed: May 2, 2016

(65) Prior Publication Data

US 2016/0244412 A1    Aug. 25, 2016

Related U.S. Application Data

(63) Continuation-in-part of application No. PCT/IN2014/000694, filed on Oct. 31, 2014.

(30) Foreign Application Priority Data

Nov. 1, 2013  (IN) .......................... 3251/DEL/2013

(51) Int. Cl.
    *C07D 231/14*    (2006.01)
(52) U.S. Cl.
    CPC .................. *C07D 231/14* (2013.01)
(58) Field of Classification Search
    None
    See application file for complete search history.

(56) References Cited

U.S. PATENT DOCUMENTS 6,265,351 B1 * 7/2001 Porta ...................... A01N 43/56
                                                  504/263

FOREIGN PATENT DOCUMENTS

EP        2128139       12/2009
WO    WO 2006/047504     5/2006

OTHER PUBLICATIONS

International Search Report and Written Opinion issued in PCT/IN2014/000694, dated Apr. 1, 2015.

* cited by examiner

*Primary Examiner* — Kamal Saeed
(74) *Attorney, Agent, or Firm* — Norton Rose Fulbright US LLP

(57) ABSTRACT

The present invention provides a process for the preparation of N-alkylated fluorine-containing pyrazolecarboxylic acid derivatives of Formula I. The present invention further provides a pyrazole compound of formula IIIa.

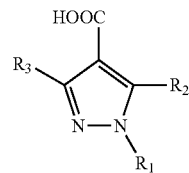

Formula I

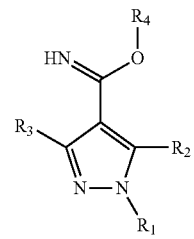

Formula IIIa

17 Claims, No Drawings

PROCESS FOR THE PREPARATION OF PYRAZOLE DERIVATIVES

CROSS-REFERENCE TO RELATED APPLICATIONS

This application is a continuation-in-part of International Application No. PCT/IN2014/000694 filed Oct. 31, 2014, which claims priority to Indian Patent Application No. 3251/DEL/2013 filed Nov. 1, 2013. The entire contents of each of the above-referenced disclosures is specifically incorporated by reference herein without disclaimer.

FIELD OF THE INVENTION

The present invention provides a process for the preparation of N-alkylated fluorine-containing pyrazolecarboxylic acid derivatives. The present invention further provides a pyrazole compound of formula IIIa.

BACKGROUND OF THE INVENTION

The N-alkylated fluorine-containing pyrazolecarboxylic acid derivatives, for example 3-difluoromethyl-1-methyl-1H-pyrazole-4-carboxylic acid, are valuable intermediates in the field of medicine and agricultural chemicals. The EP Patent No. 2,128,139 B1 provides a process for the preparation of N-alkylated fluorine-containing pyrazolecarboxylic acid of Formula I. The process involves reacting N-alkylated fluorine-containing pyrazolecarbonitrile of Formula II with water.

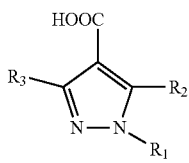

Formula I

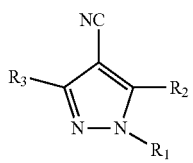

Formula II wherein:

$R_1$ represents an alkyl group having 1 to 6 carbon atoms, a cycloalkyl group having 3 to 6 carbon atoms or an arylalkyl group which may be substituted; $R_2$ represents a hydrogen, an alkyl group having 1 to 6 carbon atoms, a cycloalkyl group having 3 to 6 carbon atoms or an arylalkyl group which may be substituted or aryl group which may be substituted; and $R_3$ represents an alkyl group having 1 to 6 carbon atoms which is substituted by at least one fluorine atom.

Object of the Invention

It is an object of the present invention to provide a process for the preparation of pyrazole compound of Formula I,

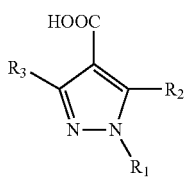

Formula I said process comprising:
a) reacting a compound of Formula II with a compound of Formula IV and hydrochloric acid to obtain a compound of Formula III; and
b) reacting the compound of Formula III with water to obtain the compound of Formula I.

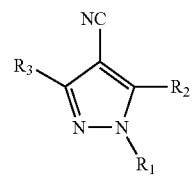

Formula II

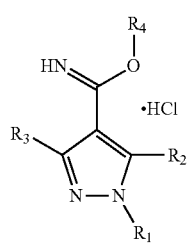

Formula III $R_4$—OH  Formula IV wherein:

$R_1$ represents an alkyl group having 1 to 6 carbon atoms, a cycloalkyl group having 3 to 6 carbon atoms or an arylalkyl group which is optionally substituted;

$R_2$ represents a hydrogen, an alkyl group having 1 to 6 carbon atoms, a cycloalkyl group having 3 to 6 carbon atoms or an arylalkyl group which is optionally substituted or aryl group which is optionally substituted;

$R_3$ represents an alkyl group having 1 to 6 carbon atoms which is substituted by at least one halogen atom;

$R_4$ represents an alkyl group having 1 to 6 carbon atoms; and

Halogen atom is selected from the group consisting of iodine, bromine, chlorine and fluorine.

Yet another object of the present invention is to provide a pyrazole compound of Formula IIIa or its salts thereof

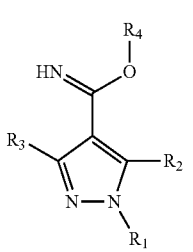

Formula IIIa wherein:

R₁ represents an alkyl group having 1 to 6 carbon atoms, a cycloalkyl group having 3 to 6 carbon atoms or an arylalkyl group which is optionally substituted;

R₂ represents hydrogen, an alkyl group having 1 to 6 carbon atoms, a cycloalkyl group having 3 to 6 carbon atoms or an arylalkyl group which is optionally substituted or aryl group which is optionally substituted;

R₃ represents an alkyl group having 1 to 6 carbon atoms which is substituted by at least one halogen atom;

R₄ represents an alkyl group having 1 to 6 carbon atoms; and

Halogen atom is selected from the group consisting of iodine, bromine, chlorine and fluorine.

SUMMARY OF THE INVENTION

The present invention provides a process for the preparation of pyrazole compound of Formula I,

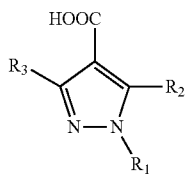

Formula I said process comprising:
a) reacting a compound of Formula II with a compound of Formula IV and hydrochloric acid to obtain a compound of Formula III; and
b) reacting the compound of Formula III with water to obtain the compound of Formula I.

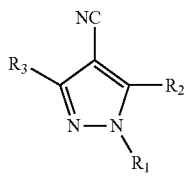

Formula II

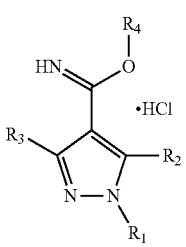

Formula III

R₄—OH

Formula IV wherein:

R₁ represents an alkyl group having 1 to 6 carbon atoms, a cycloalkyl group having 3 to 6 carbon atoms or an arylalkyl group which is optionally substituted;

R₂ represents a hydrogen, an alkyl group having 1 to 6 carbon atoms, a cycloalkyl group having 3 to 6 carbon atoms or an arylalkyl group which is optionally substituted or aryl group which is optionally substituted;

R₃ represents an alkyl group having 1 to 6 carbon atoms which is substituted by at least one halogen atom;

R₄ represents an alkyl group having 1 to 6 carbon atoms; and

Halogen atom is selected from the group consisting of iodine, bromine, chlorine and fluorine.

In an embodiment of the invention, the reaction between the compound of Formula II with the compound of Formula IV and hydrochloric acid is taking place at a temperature in the range of about −20° C. to about 50° C.

In another embodiment of the invention, the reaction between the compound of Formula II with the compound of Formula IV and hydrochloric acid is taking place for a time period in the range of about 15 minutes to about 24 hours.

In yet another embodiment of the invention, wherein the reaction between the compound of Formula II with the compound of Formula IV and hydrochloric acid is taking place in the presence of a solvent.

In yet another embodiment of the invention, the solvent is selected from the group consisting of aromatic solvent, ester solvent, ether solvent and chlorinated solvent.

In an embodiment of the invention, the aromatic solvent is selected from the group consisting of toluene and xylene.

In another embodiment of the invention, wherein the reaction between the compound of Formula III and water is taking place at a temperature in the range of about 25° C. to about 150° C.

In yet another embodiment of the invention, the reaction between the compound of Formula III and water is taking place for a time period in the range of about 15 minutes to about 36 hours.

In one another embodiment of the invention, the present invention provides a pyrazole compound of Formula IIIa or its salts thereof:

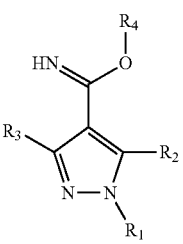

Formula IIIa wherein:

R₁ represents an alkyl group having 1 to 6 carbon atoms, a cycloalkyl group having 3 to 6 carbon atoms or an arylalkyl group which is optionally substituted;

R₂ represents hydrogen, an alkyl group having 1 to 6 carbon atoms, a cycloalkyl group having 3 to 6 carbon atoms or an arylalkyl group which is optionally substituted or aryl group which is optionally substituted;

R₃ represents an alkyl group having 1 to 6 carbon atoms which is substituted by at least one halogen atom;

R₄ represents an alkyl group having 1 to 6 carbon atoms; and

Halogen atom is selected from the group consisting of iodine, bromine, chlorine and fluorine.

In an embodiment of the invention, the compound is selected from the group consisting of
methyl 3-(difluoromethyl)-1-methyl-1H-pyrazole-4-carboximidoate,
ethyl 3-(difluoromethyl)-1-methyl-1H-pyrazole-4-carboximidoate, propyl 3-(difluoromethyl)-1-methyl-1H-pyrazole-4-carboximidoate and
n-butyl 3-(difluoromethyl)-1-methyl-1H-pyrazole-4-carboximidoate or their salt thereof.

DETAILED DESCRIPTION OF THE INVENTION

The present invention provides a process for the preparation of pyrazole compound of Formula I, said process comprising:
a) reacting a compound of Formula II with a compound of Formula IV and hydrochloric acid to obtain the compound of Formula III; and

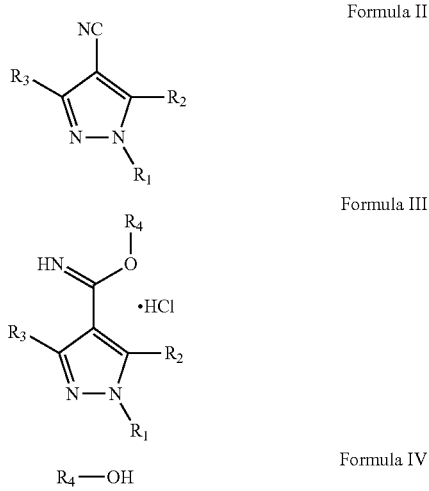

b) reacting the compound of Formula III with water to obtain the compound of Formula I.

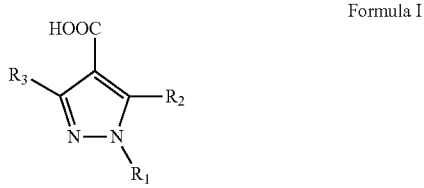

wherein:
$R_1$ represents an alkyl group having 1 to 6 carbon atoms, a cycloalkyl group having 3 to 6 carbon atoms or an arylalkyl group which is optionally substituted;
$R_2$ represents hydrogen, an alkyl group having 1 to 6 carbon atoms, a cycloalkyl group having 3 to 6 carbon atoms or an arylalkyl group which is optionally substituted or aryl group which is optionally substituted;
$R_3$ represents an alkyl group having 1 to 6 carbon atoms which is substituted by at least one halogen atom;
$R_4$ represents an alkyl group having 1 to 6 carbon atoms; and
Halogen atom is selected from the group consisting of iodine, bromine, chlorine and fluorine.
The compound of Formula II may be prepared by any method known in the art, preferably, by method known in EP Patent No. 2,128,139 B1.

The term "about," as used herein, refers to a value which is ±10% of the mentioned value, however where the percentage is provided in such a case the maximum value will be 100%.

The reaction of compound of Formula II with the compound of Formula IV and hydrochloric acid may take place in the presence of a solvent. The solvent may be selected from the group consisting of aromatic solvent, ester solvent, ether solvent and chlorinated solvent or mixture thereof.

The aromatic solvent may be selected from the group consisting of toluene and xylene or mixture thereof.

The chlorinated solvent may be selected from the group consisting of dichloromethane, chloroform and carbon tetrachloride or mixture thereof.

The ester solvent may be selected from the group consisting of ethyl acetate, methyl acetate, methyl propionate, ethyl acetoacetate and ethyl butyrate or mixture thereof.

The ether solvent may be selected from the group consisting of diethyl ether, di-tert-butyl ether, dimethoxyethane, dimethoxymethane, 1,4-dioxane, ethyl tert-butyl ether, methoxyethane, tetrahydrofuran, tetrahydropyran, and cyclopentyl methyl ether or mixture thereof.

The hydrochloric acid may be in solution phase or in gaseous phase.

The reaction of compound of Formula II with the compound of Formula IV and hydrochloric acid may take place in the range of about 15 minutes to about 24 hours, preferably, in the range of about 3 hours to about 12 hours at a temperature in the range of about −20° C. to about 50° C.

The compound of Formula III may be isolated from the reaction mixture by the method known in the prior arts, preferably, the compound of Formula III may be isolated from the reaction mixture by filtration, decantation, precipitation, distillation, evaporation, layer separation, crystallization and condensation or mixture thereof.

The compound of Formula III may be taken in-situ for conversion to compound of Formula I.

The compound of Formula III may be converted to compound of Formula I by treatment with water.

The treatment of compound of Formula III with water may take place at a temperature in the range of about 25° C. to about 150° C., preferably, at a temperature in the range of about 60° C. to about 120° C.

The treatment of compound of Formula III with water may take place at a temperature in the range of for about 15 minutes to about 36 hours, preferably, for a time period in the range of about 3 hours to about 15 hours.

The compound of Formula I may be isolated from the reaction mixture by filtration, decantation, precipitation, distillation, evaporation, layer separation, crystallization and condensation or mixture thereof.

The compound of Formula I has a purity of greater than about 98%.

The present invention further provides a pyrazole compound of Formula IIIa or its salts thereof:

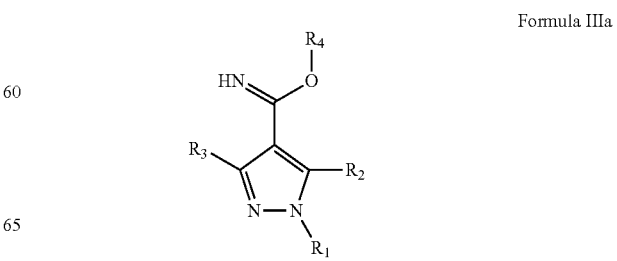

wherein:
R₁ represents an alkyl group having 1 to 6 carbon atoms, a cycloalkyl group having 3 to 6 carbon atoms or an arylalkyl group which is optionally substituted;

R₂ represents hydrogen, an alkyl group having 1 to 6 carbon atoms, a cycloalkyl group having 3 to 6 carbon atoms or an arylalkyl group which is optionally substituted or aryl group which is optionally substituted;

R₃ represents an alkyl group having 1 to 6 carbon atoms which is substituted by at least one halogen atom;

R₄ represents an alkyl group having 1 to 6 carbon atoms; and

Halogen atom is selected from the group consisting of iodine, bromine, chlorine and fluorine.

The present invention further provides a compound of Formula IIIa or its salt, for example methyl 3-(difluoromethyl)-1-methyl-1H-pyrazole-4-carboximidoate,
ethyl 3-(difluoromethyl)-1-methyl-1H-pyrazole-4-carboximidoate,
propyl 3-(difluoromethyl)-1-methyl-1H-pyrazole-4-carboximidoate, and
n-butyl 3-(difluoromethyl)-1-methyl-1H-pyrazole-4-carboximidoate or their salts.

The salt of Formula IIIa may be an organic salt or an inorganic salt.

The salt represents sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, formate, oxalate, malonate, succinate, suberate, sebacate, fumarate, maleate, methanesulfonate, mandelate and the like salts.

The present invention further provides a compound of Formula IIIa or its salts having purity greater than about 95%.

The present invention further provides the use of compound of Formula IIIa or its salt for the preparation of compound of Formula I.

The present invention provides a process for the preparation of pyrazole compound of Formula I,

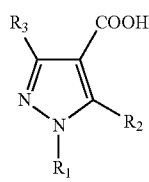

Formula I wherein R₁ represents an alkyl group having 1 to 6 carbon atoms, a cycloalkyl group having 3 to 6 carbon atoms or an arylalkyl group which is optionally substituted;

R₂ hydrogen, alkyl group having 1 to 6 carbon atoms, a cycloalkyl group having 3 to 6 carbon atoms or an arylalkyl group which is optionally substituted, or an aryl group which is optionally substituted;

R₃ represents an alkyl group having 1 to 6 carbon atoms which is substituted by at least one halogen atom; and halogen atom selected from fluorine, chlorine, bromine and iodine said process comprising:
(a) contacting a compound of Formula V with a ferric chloride to obtain a compound of Formula VI;

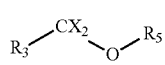

Formula V

R₃ is defined as above

R₅ represents an alkyl group having 1 to 6 carbon atoms

X is halogen atom selected from fluorine, chlorine, bromine and iodine

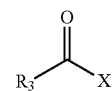

Formula VI (b) contacting the compound of Formula VI with a compound of Formula VII to obtain a compound of Formula VIII;

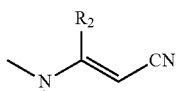

Formula VII

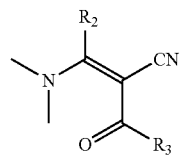

Formula VIII

R₂ and R₃ defined as above (c) contacting the compound of Formula VIII with a compound of Formula IX to obtain a compound of Formula II;

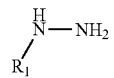

Formula IX

R₁ defined as above (d) contacting the compound of Formula II with a compound of Formula IV and hydrochloric acid to obtain a compound of Formula III; and

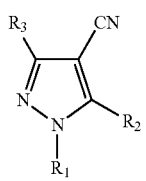

Formula II

R₁, R₂ and R₃ defined as above

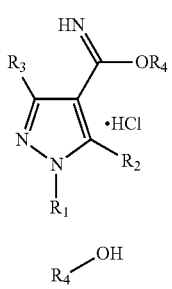

Formula III

Formula IV $R_1$, $R_2$ and $R_3$ defined as above

R4 represents an alkyl group having 1 to 6 carbon atoms;
(e) contacting the compound of Formula III with water to obtain the compound of Formula I;
wherein the compounds of Formula VI, VIII, II, and III are not isolated from the reaction mixture.

An embodiment of the present invention provides that step (b) takes place in the presence of an organic solvent and a base.

In an embodiment of the present application, step (b) takes place at a temperature in the range of about 10° C. to about 15° C.

In another embodiment of the present invention step (c) takes place in the presence of a base, water and organic solvent.

In yet another embodiment of the present invention, the reaction between the compound of Formula II with the compound of Formula IV and hydrochloric acid is taking place at a temperature in the range of about −20° C. to about 50° C.

In an embodiment of the present invention the reaction between the compound of Formula II with the compound of Formula IV and hydrochloric acid is taking place for a time period in the range of about 15 minutes to about 24 hours.

In still another embodiment of the present invention the reaction between the compound of Formula II with the compound of Formula IV and hydrochloric acid is taking place in the presence of a solvent.

In another embodiment of the present invention the solvent is selected from the group consisting of aromatic solvent, ester solvent, ether solvent and chlorinated solvent or mixture thereof.

In yet another embodiment of the present invention the aromatic solvent is selected from the group consisting of toluene and xylene or mixture thereof.

In another embodiment of the present invention the reaction between the compound of Formula III and water is taking place at a temperature in the range of about 25° C. to about 150° C.

In still another embodiment of the present invention the reaction between the compound of Formula III and water is taking place for a time period in the range of about 15 minutes to about 36 hours.

In an embodiment of the present invention the base used in step (b) is triethylamine.

In yet another embodiment of the present invention the base used in step (c) is NaOH.

In another embodiment of the present invention the organic solvent is toluene.

The present invention provides a process for the preparation of 3-(difluoromethyl)-1-methyl-1H-pyrazole-4-carboxylic acid, said process comprising:

(a) contacting 1,1,2,2-tetrafluoro-1-methoxyethane with ferric chloride on carbon pellets to obtain a first mixture;

(b) contacting the first mixture as obtained in step (a) with 3-(dimethylamino) acrylonitrile to obtain a second mixture;

(c) contacting monomethylhydrazine with the second mixture to obtain a third mixture comprising an aqueous layer and an organic layer;

(d) contacting methanol and hydrochloric acid with the organic layer of step (c) to obtain hydrochloric acid salt of 3-(difluoromethyl)-1-methyl-1-H-pyrazole carboximidoate;

(e) converting hydrochloric acid salt of methyl 3-(difluoromethyl)-1-methyl-1-H-pyrazole carboximidoate to 3-(difluoromethyl)-1-methyl-1H-pyrazole-4-carboxylic acid; and (f) isolating 3-(difluoromethyl)-1-methyl-1H-pyrazole-4-carboxylic acid from step (f).

The present invention provides a compound of formula IIIa or its salts thereof

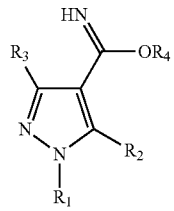

Formula IIIa wherein:

$R_1$ represents an alkyl group having 1 to 6 carbon atoms, a cycloalkyl group having 3 to 6 carbon atoms or an arylalkyl group which is optionally substituted;

$R_2$ represents hydrogen, an alkyl group having 1 to 6 carbon atoms, a cycloalkyl group having 3 to 6 carbon atoms or an arylalkyl group which is optionally substituted or aryl group which is optionally substituted;

$R_3$ represents an alkyl group having 1 to 6 carbon atoms which is substituted by at least one halogen atom; halogen atom is selected from the group consisting of iodine, bromine, chlorine and fluorine; and $R_4$ represents an alkyl group having 1 to 6 carbon atoms.

In an embodiment of the present application the compound is selected from the group consisting of:

methyl 3-(difluoromethyl)-1-methyl-1H-pyrazole-4-carboximidoate, ethyl 3-(difluoromethyl)-1-methyl-1H-pyrazole-4-carboximidoate, propyl 3-(difluoromethyl)-1-methyl-1H-pyrazole-4-carboximidoate, n-butyl 3-(difluoromethyl)-1-methyl-1H-pyrazole-4-carboximidoate, and salt thereof.

While the present invention has been described in terms of its specific embodiments, certain modifications and equivalents will be apparent to those skilled in the art and are intended to be included within the scope of the present invention.

EXAMPLES

Example 1

Preparation of 3-(difluoromethyl)-1-methyl-1H-pyrazole-4-carboxylic acid

Under nitrogen atmosphere, a U-tube was filled with 300 g of $FeCl_3$ on carbon pellets. The above U tube was heated up to 235° C. and moisture therein was removed by passing nitrogen. The catalyst was activated by passing 1,1,2,2-tetrafluoro-1-methoxyethane vapors produced at 180° C.

1,1,2,2-tetrafluoro-1-methoxyethane (75.6 g) was vaporized and passed through activated $FeCl_3$ on carbon. The outlet gas was purged in a solution containing 50 g of 3-(dimethylamino)acrylonitrile dissolved in toluene (120 g) and triethylamine (15.8 g) at 10° C. to 15° C. over a period of 2 h to obtain reaction mass. The aqueous monomethylhydrazine (40%, 59.4 g), sodium hydroxide (10.54 g) and toluene (407 g) were taken together in a separate reaction vessel and mixture was cooled to 0° C. This mixture was added to the reaction mass over a period of 1 h at 0° C. The reaction mixture was stirred for 2 h at 0° C. The aqueous layer was removed and 70 g of methanol was added to the organic layer. The dry hydrochloric acid gas (70 g) was passed into the reaction mixture and was stirred for about 5 h to about 10 h to obtain hydrochloric acid salt of methyl 3-(difluoromethyl)-1-methyl-1-H-pyrazole carboximidoate.

1a. The water (180 g) was added to the hydrochloric acid salt of methyl 3-(difluoromethyl)-1-methyl-1-H-pyrazole carboximidoate in toluene and the mixture was heated to 110° C. The toluene was removed azeotropically and methanol was distilled out from the reaction mixture. The reaction mixture was cooled to 15° C., filtered and dried to obtain the title compound.

Purity: 99% (HPLC)

1b. The hydrochloric acid salt of methyl 3-(difluoromethyl)-1-methyl-1-H-pyrazole carboximidoate in toluene was heated to remove methanol and hydrochloride. The water (105 g) was added to the mixture followed by sodium hydroxide solution (30%, 149 g). The mixture was refluxed for 4 h, neutralized with hydrochloride acid solution (35%, 125 g). The mass was cooled to 15° C. and filtered to obtain the title compound.

Purity: 99% (HPLC).

We claim:

1. A process for the preparation of pyrazole compound of Formula I,

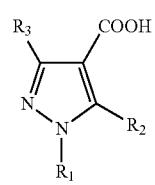

Formula I wherein $R_1$ represents an alkyl group having 1 to 6 carbon atoms, a cycloalkyl group having 3 to 6 carbon atoms or an arylalkyl group which is optionally substituted;
$R_2$ hydrogen, alkyl group having 1 to 6 carbon atoms, a cycloalkyl group having 3 to 6 carbon atoms or an arylalkyl group which is optionally substituted, or an aryl group which is optionally substituted;
$R_3$ represents an alkyl group having 1 to 6 carbon atoms which is substituted by at least one halogen atom; and halogen atom selected from fluorine, chlorine, bromine and iodine said process comprising:
(a) contacting a compound of Formula V with a ferric chloride to obtain a compound of Formula VI;

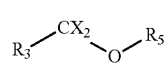

Formula V $R_3$ is defined as above;
$R_5$ represents an alkyl group having 1 to 6 carbon atoms;
X is halogen atom selected from fluorine, chlorine, bromine and iodine;

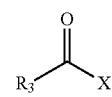

Formula VI (b) contacting the compound of Formula VI with a compound of Formula VII to obtain a compound of Formula VIII;

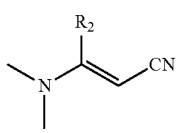

Formula VII

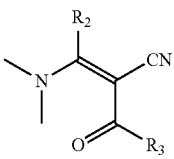

Formula VIII $R_2$ and $R_3$ defined as above;
(c) contacting the compound of Formula VIII with a compound of Formula IX to obtain a compound of Formula II;

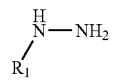

Formula IX $R_1$ defined as above;
(d) contacting the compound of Formula II with a compound of Formula IV and hydrochloric acid to obtain a compound of Formula III; and

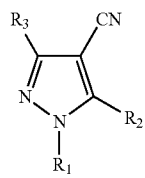

Formula II $R_1$, $R_2$ and $R_3$ defined as above;

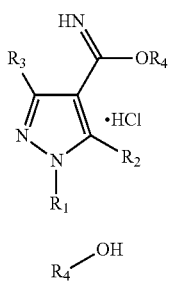

Formula III

Formula IV

R₁, R₂ and R₃ defined as above;
R4 represents an alkyl group having 1 to 6 carbon atoms;
(e) contacting the compound of Formula III with water to obtain the compound of Formula I;
wherein the compounds of Formula VI, VIII, II, and III are not isolated from the reaction mixture.

2. The process as claimed in claim 1, wherein step (b) takes place in the presence of an organic solvent and a base.

3. The process as claimed in claim 1, wherein step (b) takes place at a temperature in the range of about 10° C. to about 15° C.

4. The process as claimed in claim 1, wherein step (c) takes place in the presence of a base, water and organic solvent.

5. The process as claimed in claim 1, wherein the reaction between the compound of Formula II with the compound of Formula IV and hydrochloric acid is taking place at a temperature in the range of about −20° C. to about 50° C.

6. The process as claimed in claim 1, wherein the reaction between the compound of Formula II with the compound of Formula IV and hydrochloric acid is taking place for a time period in the range of about 15 minutes to about 24 hours.

7. The process as claimed in claim 1, wherein the reaction between the compound of Formula II with the compound of Formula IV and hydrochloric acid is taking place in the presence of a solvent.

8. The process as claimed in claim 7, wherein the solvent is selected from the group consisting of aromatic solvent, ester solvent, ether solvent and chlorinated solvent or mixture thereof.

9. The process as claimed in claim 8, wherein the aromatic solvent is selected from the group consisting of toluene and xylene or mixture thereof.

10. The process as claimed in claim 1, wherein the reaction between the compound of Formula III and water is taking place at a temperature in the range of about 25° C. to about 150° C.

11. The process as claimed in claim 1, wherein the reaction between the compound of Formula III and water is taking place for a time period in the range of about 15 minutes to about 36 hours.

12. The process as claimed in claim 1, wherein the base used in step (b) is triethylamine.

13. The process as claimed in claim 1, wherein the base used in step (c) is NaOH.

14. The process as claimed in claim 1, wherein the organic solvent is toluene.

15. A process for the preparation of 3-(difluoromethyl)-1-methyl-1H-pyrazole-4-carboxylic acid, said process comprising:
(a) contacting 1,1,2,2-tetrafluoro-1-methoxyethane with ferric chloride on carbon pellets to obtain a first mixture;
(b) contacting the first mixture as obtained in step (a) with 3-(dimethylamino) acrylonitrile to obtain a second mixture;
(c) contacting monomethylhydrazine with the second mixture to obtain a third mixture comprising an aqueous layer and an organic layer;
(d) contacting methanol and hydrochloric acid with the organic layer of step (c) to obtain hydrochloric acid salt of 3-(difluoromethyl)-1-methyl-1-H-pyrazole carboximidoate;
(e) converting hydrochloric acid salt of methyl 3-(difluoromethyl)-1-methyl-1-H-pyrazole carboximidoateto 3-(difluoromethyl)-1-methyl-1H-pyrazole-4-carboxylic acid; and
(f) isolating 3-(difluoromethyl)-1-methyl-1H-pyrazole-4-carboxylic acid from step (f).

16. A compound of Formula IIIa or its salts thereof

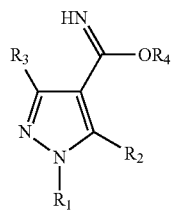

Formula IIIa wherein:
R₁ represents an alkyl group having 1 to 6 carbon atoms, a cycloalkyl group having 3 to 6 carbon atoms or an arylalkyl group which is optionally substituted;
R₂ represents hydrogen, an alkyl group having 1 to 6 carbon atoms, a cycloalkyl group having 3 to 6 carbon atoms or an arylalkyl group which is optionally substituted or aryl group which is optionally substituted;
R₃ represents an alkyl group having 1 to 6 carbon atoms which is substituted by at least one halogen atom; halogen atom is selected from the group consisting of iodine, bromine, chlorine and fluorine; and
R₄ represents an alkyl group having 1 to 6 carbon atoms.

17. The compound as claimed in claim 16, wherein the compound is selected from the group consisting of:
methyl 3-(difluoromethyl)-1-methyl-1H-pyrazole-4-carboximidoate,
ethyl 3-(difluoromethyl)-1-methyl-1H-pyrazole-4-carboximidoate,
propyl 3-(difluoromethyl)-1-methyl-1H-pyrazole-4-carboximidoate,
n-butyl 3-(difluoromethyl)-1-methyl-1H-pyrazole-4-carboximidoate, and salt thereof.

* * * * *